(12) United States Patent
McGlone (10) Patent No.: US 9,480,689 B1
(45) Date of Patent: Nov. 1, 2016

(54) PHEROMONE COMPOSITION TO STIMULATE REPRODUCTION IN FEMALE SUIDS AND METHODS OF USE

(71) Applicant: Texas Tech University System, Lubbock, TX (US)

(72) Inventor: John J. McGlone, Lubbock, TX (US)

(73) Assignee: Animal Biotech, LLC, Dallas, TX (US)

( * ) Notice: Subject to any disclaimer, the term of this patent is extended or adjusted under 35 U.S.C. 154(b) by 0 days.

(21) Appl. No.: 14/943,607

(22) Filed: Nov. 17, 2015

(51) Int. Cl.
*A61K 31/47* (2006.01)
*A61K 31/568* (2006.01)
*A61K 9/00* (2006.01)

(52) U.S. Cl.
CPC ........... *A61K 31/568* (2013.01); *A61K 9/0073* (2013.01); *A61K 31/47* (2013.01)

(58) Field of Classification Search
CPC ............................ A61K 31/47; A61K 31/568
See application file for complete search history.

(56) References Cited

U.S. PATENT DOCUMENTS

2006/0252738 A1* 11/2006 Avelino ............... A61K 9/1075
514/177
2013/0072570 A1* 3/2013 McGlone ................. A61K 9/12
514/703

OTHER PUBLICATIONS

The Merck Index Online, "Quinoline", revised 2013.*

* cited by examiner

*Primary Examiner* — Gina Justice
(74) *Attorney, Agent, or Firm* — Polsinelli PC (57) ABSTRACT

The present disclosure provides for compositions and methods of stimulating reproductive behavior and reproductive success and productivity in a suid, such as pigs. The composition may comprise at least one steroid hormone and a heterocyclic aromatic compound. The method comprises administering the pheromone composition to the suid for a period of time.

16 Claims, 4 Drawing Sheets

BSA = Boar Saliva Analog comprising Androstenone, Androstenol, and quinoline; Iso = Isopropyl alcohol control; A+A = Androstenone and androstenol.

FIG. 1

BSA = Boar Saliva Analog comprising Androstenone, Androstenol, and quinoline; Iso = Isopropyl alcohol control; A+A = Androstenone and androstenol.

BSA = Boar Saliva Analog comprising Androstenone, Androstenol, and quinoline; Iso = Isopropyl alcohol control; A+A = Androstenone and androstenol.

FIG. 4

PHEROMONE COMPOSITION TO STIMULATE REPRODUCTION IN FEMALE SUIDS AND METHODS OF USE

FIELD OF THE INVENTIONS

The present invention relates to a composition comprising a combination of pheromonal agents and methods of using such compositions to modify behavior in an animal. More particularly, the present disclosure is concerned with a pheromone composition comprising a combination of a heterocyclic aromatic compound and at least one androgen steroid, and the use of such composition to stimulate or induce reproductive behavior in female pigs.

BACKGROUND

Pheromone signals are known to play a major role in mammalian reproduction and behavior. In the case of pigs, females will signal when they are coming into *oestrus* and using pheromones and distinctive behavior (e.g., lordosis or standing reflex), they will solicit approaches by the male.

Early scientific literature pointed to salivary steroid molecules androstenone and androstenol as the recognized boar pheromone that is responsible for inducing reproduction in the female pig (see Melrose et al., Androgen steroids associated with boar odour as an aid to the detection of *oestrus* in pig artificial insemination, The British Veterinary Journal, 127, 497-502 (1971); see also Perry et al., Pig courtship behaviour: pheromonal property of androstene steroids in male submaxillary secretion, Animal Production, 31, 191-199 (1980)). Products such as Boarmate™ (ITSI, Canada), which contain Androstenone, have long been sold on the market to detect female pigs in heat and have been used to save time and money when breeding pigs.

However, the synthetic products presently on the market are not always successful in replicating boar saliva to induce sow reproductive behavior and performance. As a result, determining when female pigs are in heat becomes increasingly labor intensive, costly, and inefficient, as more boars may be needed to be kept on site, females in heat may be difficult to find, and reproductive successes may be decreased.

Accordingly, there is a need within the industry for a synthetic boar saliva composition that has a greater likelihood of inducing reproductive behavior and increasing reproductive success and productivity in female pigs.

SUMMARY OF THE PRESENT INVENTION

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

It is an object of the present invention to provide novel methods and compositions for the inducement of reproductive behavior in female suids comprising a combination of a heterocyclic aromatic compound and at least one androgen steroid.

The composition of the invention preferably comprises the combination of Androstenone, androstenol, and quinoline and may optionally include other ingredients as necessary or desired, depending on the form and intended use of the final product. Such optional ingredients can include, but are not limited to, carriers such as water, alcohols, solvents, and the like; fragrances, coloring agents, preservatives, antioxidants, and the like. Examples of the resultant product include, but are not limited to, a spray, a diffuser, or an aerosol. Alternatively, the resultant product may be a foam, a dip, a wipe, a cream, a gel, or a lotion.

Another object of the present invention is to provide a method for inducing reproductive behavior and reproductive success and productivity in a female suid, the method comprising administering a composition comprising the combination of a heterocyclic aromatic compound, such as quinoline, and at least one androgen steroid, such as Androstenone and androstenol, in an amount effective to induce reproductive behavior in a female suid.

Various objects and advantages of this use will become apparent from the following description taken in conjunction with the accompanying drawings wherein, by way of illustration and example, certain embodiments of this disclosure are set forth.

DETAILED DESCRIPTION

The composition of the present disclosure comprises a combination of pheromone and aromatic compounds, the combination collectively referred to herein as "pheromonal agents", which composition has been found to be useful and effective in inducing or stimulating reproductive behavior in female suids.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification the drawings, the chemical structures, and descriptions, which forms a part of this disclosure. Any description of any R-group or chemical substituent, alone or in any combination, may be used in any chemical Formula described herein, and Formulae include all conformational and stereoisomers, including diastereomers, epimers, and enantiomers. Moreover any feature of a composition disclosed herein may be used in combination with any other feature of a composition disclosed herein.

I. Pheromone Composition

The composition of the present disclosure generally comprises a combination of pheromonal agents. The unique combination of pheromonal agents disclosed herein has surprisingly been found to be extremely effective in inducing reproductive behaviors in female suids.

The pheromonal agents used in the compositions of the present invention comprise at least one steroid hormone. Steroid hormones can be grouped into five groups based on the receptors to which they bind: glucocorticoids, mineralocorticoids, androgens, estrogens, and progestogens. Steroid hormones useful in the present invention may be natural or synthetic. Preferably, the steroid hormone comprises at least one androgen steroid, which may be selected from the group consisting of androstenone, androstenol, androstadienone, estratetraenol, and combinations thereof. Preferably, the androgen steroid is a combination of androstenone and androstenol.

Generally, the amount of steroid hormone present in the formulation is at least 0.0000001% (w/w) of the total composition. In one embodiment, the concentration of steroid hormone present in the composition ranges from between about 0.0000001% to about 10% (w/w). In another embodiment, the concentration of steroid hormone present in the composition ranges from between about 0.0001% to about 5% (w/w). Preferably, the concentration of steroid hormone present in the composition ranges from between about 0.0001% to about 1% (w/w) and most preferably the concentration of steroid hormone present in the composition is about 0.0008% (w/w).

The pheromonal agents which are present in the composition additionally comprise an aromatic heterocyclic compound. A preferred aromatic heterocyclic compound for use in the present invention is quinoline. The amount of aromatic heterocyclic compound present in the formulation is at least 0.0000001% (w/w) of the total composition. In one embodiment, the concentration of aromatic heterocyclic compound in the composition ranges from between about 0.0000001% to about 10% (w/w). In another embodiment, the concentration of aromatic heterocyclic compound in the composition ranges from between about 0.0001% to about 5% (w/w). Preferably, the concentration of aromatic heterocyclic compound present in the composition ranges from between about 0.0001% to about 1% (w/w) and most preferably the concentration of aromatic heterocyclic compound in the composition is about 0.0004% (w/w).

In addition to the pheromonal agents, the composition may optionally contain one or more additional components such as solvents, propellants, surface-active agents, emulsifiers or thickeners, preservatives, and fragrances.

In one embodiment, the composition may include at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. Suitable alcohols include ethanol, propanol, isopropanol, butanol, pentanol, hexanol, heptanol, octanol, and phenyl ethyl alcohol. In one embodiment, the alcohols may comprise ethanol, isopropanol, butanol, and phenyl ethyl alcohol. In exemplary embodiments, the solvent comprises isopropanol. An alcohol solvent can be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In an exemplary embodiment, the solvent may be a combination of water and an alcohol selected from ethanol or isopropanol. In a one embodiment, the amount of solvent present in the composition may range from between about 0.5% and 99.99% (w/w) of the total composition. The amount of water present in the composition may range from between about 70% and about 99.99% (w/w) of the total composition, for example between about 80% and about 98.5% (w/w) of the total composition. The amount of alcohol present in the composition may range from between about 1% and about 20% (w/w) of the total composition, for example from between about 1.5% and about 10% (w/w) of the total composition.

The composition may additionally include a propellant. Suitable propellants include chlorofluorocarbons (CFC) such as trichloromonofluoromethane, dichlorodifluoromethane, and dichlorotetrafluoroethane; hydrochlorofluorocarbons (HCFC) or hydrofluoro-carbons (HFC) such as chlorodifluoromethane, trifluoromonofluoroethane, chlorodifluoro-ethane, difluoroethane, and heptafluoropropane; hydrocarbons such as propane, butane, and isobutene; and other compressed gases such as nitrogen, carbon dioxide, and nitrous oxide, as well as combinations of any of the above-described propellants. In one embodiment, the propellant may be propane. In another embodiment, the propellant may be 1,1-difluoroethane. The propellant may not comprise an inert gas of the tumorigenic compound class, which includes 1,1,1,2-tetrafluoroethane, chlorodifluoromethane, and dichlorodifluoromethane. The propellant may have a flashpoint of less than about −50° C. Generally, when a propellant is included in the composition, such may range from between about 75% to about 99.99% (w/w) of the total composition, for example between about 85% and about 99.99% (w/w) of the total composition, or between about 95% and about 99.99% (w/w) of the total composition.

The composition may optionally include one or more surfactants. Surfactants are generally used to prepare compositions formulated as emulsions. Either water-in-oil or oil-in-water emulsions may be formulated. Examples of suitable surfactants include nonionic ethoxylated and non-ethoxylated surfactants, abietic acid, almond oil PEG, beeswax, butylglucoside caprate, $C_{18}$-$C_{36}$ acid glycol ester, $C_9$-$C_{15}$ alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-$C_{12}$-$C_{13}$ pareth-3 sulfate, tri-$C_{12}$-$C_{15}$ pareth-6 phosphate, and trideceths.

In certain applications, it may be desirable to thicken the composition. Suitable thickening or viscosity increasing agent include acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, isopropyl palmitate, magnesium alginate, methylcellulose, microcrystalline cellulose, pectin, various PEGs, polyacrylic acid, polymethacrylic acid, polyvinyl alcohol, various PPGs, sodium acrylates copolymer, sodium carrageenan, xanthan gum, and yeast beta-glucan. When present, the amount of thickener may range from between about 1% to about 30% (w/w) of the total composition, for example between about 5% to about 20% (w/w) of the total composition, or from between about 10% to about 15% (w/w) of the total composition.

The composition may additionally comprise an emulsifier or thickening agent, such as distilled mono and di-glycerides, propylene glycol monoesters, sodium stearoyl-2-lactylate, polysorbate 60, lecithin, hydroxylated lecithin, lanolin, and any other emulsifier known and used in the industry.

The composition may additionally comprise a fragrance. The fragrance may be any fragrance that provides a desired odor masking effect without substantially interfering with the essential properties of the composition. Although a variety of fragrances may be employed without departing from the scope of the present disclosure, suitable fragrances include floral essences, citrus blossoms, oil or extracts of conifers, or spices. Examples of floral essences include rose, lilac, lavender, *gardenia*, and jasmine. Suitable citrus blossoms include orange and lemon, and suitable oil or extracts of conifers include pine and juniper. Generally, fragrance may comprise between about 0.25% and about 1% (w/w) of the total composition.

II. Routes of Administration

Mammals, including pigs and other suids, have several anatomical organs that receive olfactory signals. The two most dominant "smell" organs are the main olfactory epithelium (MOE) and the vomeronasal organ (VNO). Other sensory fibers in the nasal cavity can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons.

Administration of the composition to a subject female suid is typically accomplished through any method allowing for delivery of an effective amount of the composition via inhalation by the animal. Such methods of administration include, for example, placing or distributing the composition in the environment of the suid, either by applying (e.g. spraying or wiping) the composition to surfaces in the living environment of the suid or directly onto the suid, such as to its facial region or head. For example, the pheromone composition may be administered topically to an suid using an aerosol, pump spray, foam, collar, wipe, dip, liquid, gel, lotion, and/or cream.

The term "effective amount" describes an amount of pheromonal agent present in a composition sufficient to produce a noticeable effect, for example the engaging in reproductive behaviors by the subject suid, as determined according to behavioral observations described herein. The effective amount will depend on factors such as individual animal parameters including age, physical condition, size and weight; concurrent treatments; the frequency of treatment; or the mode of administration. These factors are well known to those of ordinary skill in the art.

In one embodiment, the pheromonal agents can be combined with a solvent to form a liquid solution and the liquid solution can be further prepared in various formulations suitable for delivery to the suid by inhalation. For example, liquid solutions can be further prepared according to methods well known in the art such as a pump spray, aerosol, gel, foam, cream, lotion, gel, or diffuser.

In an exemplary embodiment, the pheromonal agents are dissolved or diluted in a nonaqueous organic solvent or solvent mixture to form a solution for incorporation into a pump spray. An exemplary pump spray solution may comprise about 0.0012% (w/w) pheromonal agents, about 5% (w/w) isopropyl alcohol, about 3.5% (w/w) lanolin oil, about 91% (w/w) water. Additionally, about 0.25% (w/w) of a preservative may be added to the solution.

In a further embodiment, the pheromonal agents are dissolved or diluted with a solvent and a thickener to form a solution for use in a diffuser. An exemplary diffuser solution may comprise about 0.0012% (w/w) pheromonal agents, between about 80% to about 85% (w/w) solvent, and about 15% (w/w) thickener.

III. Methods of Using a Pheromone Composition to Induce Reproductive Behavior in a Female Suid The present disclosure is further directed to a method of using a pheromone composition to induce or stimulate reproductive behaviors or physiology in a female suid by exposing the suid to an effective amount of a composition comprising a combination of pheromonal agents, wherein the composition comprises at least about 0.00001% (w/w) of pheromonal agents within the total composition. Generally, the composition may comprise between about 0.0001% and about 1% (w/w) of pheromonal agents within the total composition.

The suid can be exposed to the composition by any method allowing inhalation by the suid over a period of time sufficient to induce reproduction, according to behavioral observations. Typically, depending on the chosen route of administration, the particular suid and situation, the exposure of the composition to the suid will be over a period of at least one second, but can also be for a period of at least one hour, for a period of between one hour and five hours, for a period of at least one day, for a period of at least one week, for a period of between one week and four weeks, for a period of at least one month, or for any period of time as may be needed to achieve a satisfactory effect.

The efficacy of the composition can be tested for example by spraying subject suids with an aerosol spray which may be dispensed via, for example, a hand operated, robotic, or automatic spray device, incorporating the composition, or by applying the composition in the form of a liquid diffuser or the like in a physical area of the suid. In any case, the composition is sufficiently volatile for the suid to inhale and thus be exposed to a sufficient amount of the composition to produce a noticeable behavioral effect.

In use, the composition comprising a combination of pheromonal agents can be implemented depending on the targeted suids. For example, an exemplary liquid spray formulation containing a combination of androstenone, androstenol, and quinoline (dissolved in a suitable solvent) can be sprayed on the suid's nostrils, face, head, in its environment, and/or in its feed, feeder, or water, such that it may be perceived through olfaction as frequently as needed to obtain the desired effect.

It should be understood that the combination of pheromonal agents used in the composition may be provided in the form of pure concentrate (100% concentration) or a diluted composition with additional excipients in the dosage form (i.e., the amount of active ingredient in the composition is less than or equal to 99.99%, and the remainder consists of inactive excipients). If diluted, the amount of pheromonal agents dispensed in the various dosage forms may range from between about 1.0 pg/mL to about 1.0 g/mL, such as between about 1.0 ng/mL to about 1.0 g/mL. One of skill in the art will appreciate that the volume of active component added to the composition will need to be adjusted to account for the dilution and to ensure the end composition comprises the appropriate final concentration of pheromonal agents. The various components of the composition may be provided in a variety of dosage forms including, but not limited to, liquid solution or suspension, emulsion, aerosol, and the like.

The compositions according to this disclosure may be applied in a variety of ways but are best applied by exposing the olfactory system by any means such as, for example, spraying a light mist directly on the facial region or in the environment of the animal. Further, the methods of the current disclosure are best accomplished by allowing the animal to inhale the composition, as the nasal cavities, sinuses, lungs and throats of animals present a large area for the aromatic molecules to be bound to an olfactory receptor. The application of the composition to the animal or the animal's environment may be repeated as often as necessary to elicit the desired effect.

DEFINITIONS

Unless otherwise defined, all technical and scientific terms used herein have the same meaning as is commonly understood by one of skill in the art to which this disclosure belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

"Suid" refers to any member of the family Suidae, hoofed mammals, order Artiodactyla, including the wild and domestic pigs, babirusas, boars, bush pigs, swine, and warthogs. Suids are stout animals with small eyes and coarse, sometimes sparse, hair. All have muzzles ending in a rounded cartilage disk used to dig for food. Some species have tusks. Suids are omnivorous and usually gregarious.

"Pheromonal agents" refers to a combination of pheromone and aromatic compounds in specific amounts which have been found to be useful and effective in inducing or stimulating reproductive behavior in female suids. Specifically, the term "pheromonal agents" as used herein refers to the combination of at least one steroid hormone, preferably androstenone and androstenol, with at least one aromatic heterocyclic compound, preferably quinoline.

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements.

Although the disclosure described herein is susceptible to various modifications and alternative iterations, specific embodiments thereof have been described in greater detail above. It should be understood, however, that the detailed description is not intended to limit the disclosure to the specific embodiments disclosed. Rather, it should be understood that the disclosure is intended to cover all modifications, equivalents, and alternatives falling within the spirit and scope of the disclosure as defined by the claim language.

EXAMPLES

Example 1

Preparation of Spray Composition Comprising Pheromonal Agents

A pump spray formulation comprising the combination of pheromonal agents androstenone, androstenol, and quinoline was prepared in accordance with the formulation set forth in Table 1.

TABLE 1

| Pump Spray Composition. | | |
|---|---|---|
| Component | % | grams |
| Androstenone | 0.0004 | 0.0004 |
| Androstenol | 0.0004 | 0.0004 |
| Quinoline | 0.0004 | 0.0004 |
| Isopropyl Alcohol | 5.0000 | 5.0000 |
| Lanolin Oil | 3.5000 | 3.5000 |
| Preservative | 0.2500 | 0.2500 |
| D.I. water | 91.2490 | 91.2490 |
| Total | 100.0000% | 100.0000 |

Example 2

Determining the Efficacy of a Spray Composition Containing Androstenone, Androstenol, and Quinoline to Induce Reproduction, and Thereby Increase Reproductive Successes and Productivity in Female Pigs This study evaluated the efficacy androstenone, androstenol, and quinoline, alone and in combination, to determine their efficacy at induction of reproduction in sows. The objective of this study was to determine if the combination of Androstenone, androstenol, and quinoline as pheromonal agents could more effectively induce reproductive behavior, and thereby increase reproductive successes and productivity in sows, compared to each pheromonal agent alone or in combination with one other pheromonal agent as illustrated in Table 2.

TABLE 2

| Pheromonal Agents and Combinations Tested. | | | | |
|---|---|---|---|---|
| | Components | | | |
| Formulation | Isopropyl Alcohol (Control) | Androstenone | Androstenol | Quinoline |
| A | X | — | — | — |
| B | — | X | — | — |
| C | — | — | X | — |
| D | — | — | — | X |
| E | — | X | X | — |
| F | — | X | — | X |
| G | — | — | X | X |
| H | — | X | X | X |

Seven (7) different spray compositions were prepared using equal proportions of androstenone, androstenol, and quinoline in various combinations, as noted in Table 2, and a control solution was prepared with only isopropyl alcohol.

All components were mixed at 4.0 µg/mL and placed in an isopropyl alcohol vehicle solution.

The efficacy of a spray composition containing Androstenone, androstenol, and quinoline was tested at a large commercial pig farm. The farm workers were observed to wean sows and breed 2-4 times per week. The animals were heat checked after feeding time, or between 7:00 am and 8:30 am, by walking 1 to 2 boars via a Boar Bot (a robotic device that pulls or pushes a live boar to provide the sow with a "boar experience") and having workers perform a back pressure test on each animal. The back pressure test is used to determine animals in the optimal state for insemination. The test consists of applying heavy pressure and rubbing on a sow's back to mimic the pressure of a boar during mating. Sows in heat will respond by locking up and arching their back, decreasing overall body and head movement, pricking their ears vertically, and grunting. Those animals that were determined to have passed the back pressure test were moved into a separate barn for artificial insemination between 9:00 AM and 10:00 AM.

Following the observation that weaned sows entered heat usually on the fourth day after weaning, the sows in each barn were sprayed with a pheromone composition or control on Day 4 using an insecticide sprayer and examined using the back pressure test. A total of 947 sows were tested. The spraying of the sows occurred between 1-2 hours before the animals were checked for signs of heat by the farm workers. After the sows were sprayed and examined, a boar was run through the barn and animals in heat were noted and moved to the artificial insemination barn. The spraying process was continued on Day 5 for the remaining animals. A total of 947 sows had their reproductive behaviors observed on Day 4 and D5 following weaning.

Figure 1:
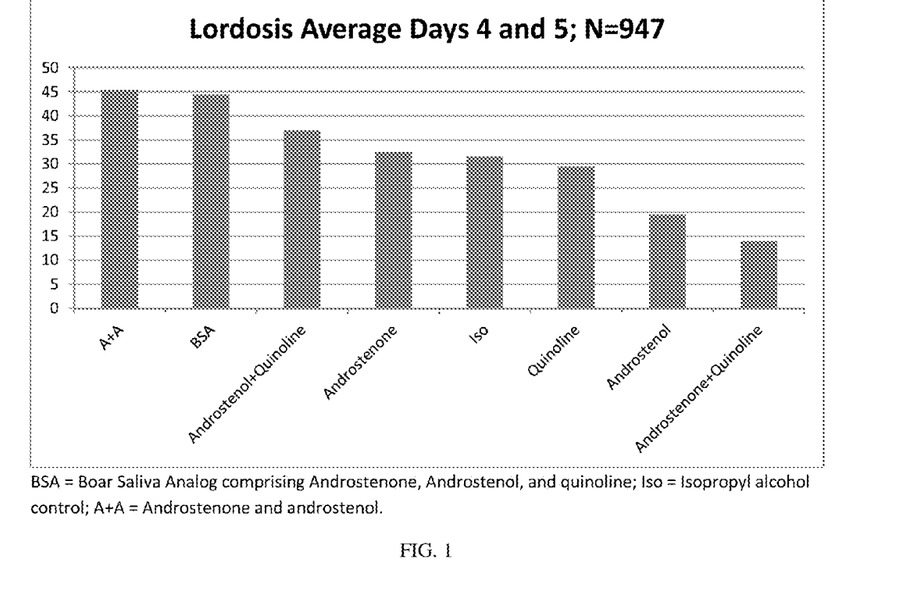
FIG. 1 is a graphic representation of effects of the control, BSA (boar saliva analog comprising Androstenone, androstenol, and quinoline), and each component of BSA alone and in other combinations on the findings for the single behavior of lordosis.
Figure 2:
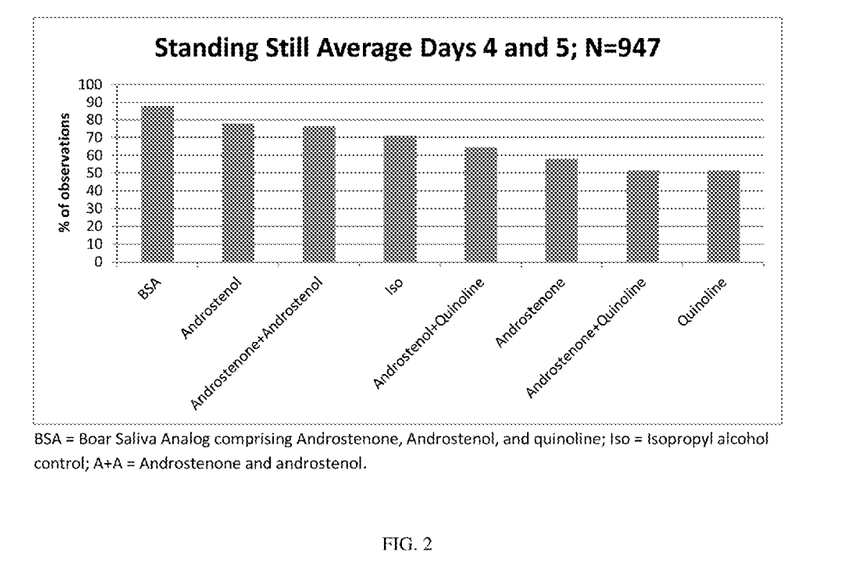
FIG. 2 is a graphic representation of effects of the control, BSA, and each component of BSA alone and in other combinations on the findings for the single behavior of standing still behavior.
Figure 3:
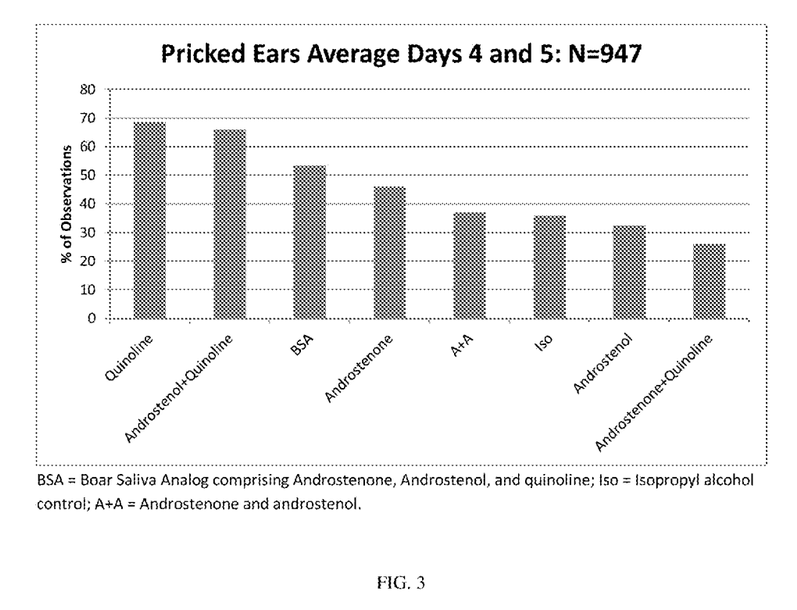
FIG. 3 is a graphic representation of effects of the control, BSA, and each component of BSA alone and in other combinations on the findings for the single behavior of expressing pricked ears.
Figure 4:
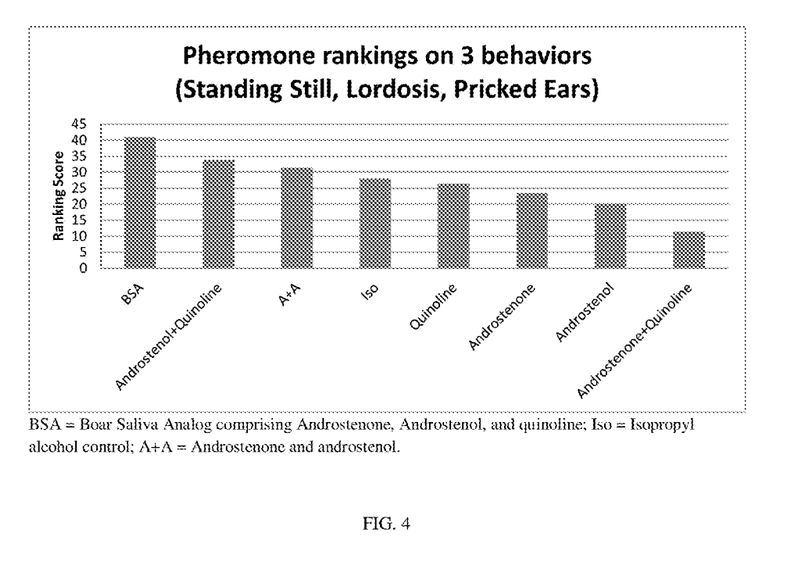
FIG. 4 is a graphic representation of the overall behavioral scores for reproductive behaviors following exposure to the control, BSA, and each component of BSA alone and in other combinations.

The three best measures to determine sow receptivity toward male insemination (standing still, lordosis, and pricked ears) were combined to create a total behavioral score. Table 3 and FIG. 1 graphically represent the findings for the single behavior of lordosis behavior. Table 4 and FIG. 2 graphically represent the findings for standing still behavior. Table 5 and FIG. 3 graphically represent data on sows expressing pricked ears. Table 6 and FIG. 4 graphically represent the overall behavioral scores for reproductive behaviors.

TABLE 3

Percentage of Animals in a Herd Displaying Lordosis Behaviors.
Lordosis.

| Formulation | Day 4 | Day 5 | Average |
|---|---|---|---|
| E | 13 | 78 | 46 |
| H | 47 | 42 | 45 |
| G | 35 | 39 | 37 |
| B | 24 | 41 | 33 |
| A | 25 | 38 | 32 |
| D | 24 | 35 | 30 |
| C | 9 | 30 | 20 |
| F | 9 | 19 | 14 |

TABLE 4

Percentage of Animals in a Herd Displaying Standing Still Behaviors.
Standing Still.

| Formulation | Day 4 | Day 5 | Average |
|---|---|---|---|
| H | 82 | 94 | 88 |
| C | 72 | 84 | 78 |
| E | 56 | 97 | 77 |
| A | 58 | 84 | 71 |
| G | 54 | 75 | 65 |
| B | 45 | 71 | 58 |
| F | 55 | 48 | 52 |
| D | 47 | 56 | 52 |

TABLE 5

Percentage of Animals Displaying Pricked Ears
Pricked Ears.

| Formulation | Day 4 | Day 5 | Average |
|---|---|---|---|
| D | 73 | 64 | 69 |
| G | 66 | 66 | 66 |
| H | 49 | 58 | 54 |
| B | 45 | 47 | 46 |
| E | 15 | 59 | 37 |
| A | 35 | 37 | 36 |
| C | 33 | 32 | 33 |
| F | 15 | 37 | 26 |

TABLE 6

Reproductive Behavioral Scores and Ranking of Scores

| Formulation | Total Score |
|---|---|
| H | 41.0 |
| G | 34.0 |
| E | 31.5 |
| A | 28.0 |
| D | 26.5 |
| B | 23.5 |
| C | 20.0 |
| F | 11.5 |

After adding the rankings across the behaviors and days, it was determined that the formulation containing androstenone, androstenol, and quinoline, in combination, demonstrated the strongest overall responses in sows. Accordingly, these results illustrate that the present invention is effective in stimulating reproductive behavior in sows, which in turn increases reproductive successes and productivity.

One skilled in the art would readily appreciate that the methods, compositions, and products described herein are representative of exemplary embodiments, and not intended as limitations on the scope of the disclosure. It will be readily apparent to one skilled in the art that varying substitutions and modifications may be made to the present disclosure disclosed herein without departing from the scope and spirit of the disclosure.

The present disclosure illustratively described herein suitably may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

What is claimed is:

1. A composition for stimulating reproductive behavior and increasing reproductive success and productivity in a female suid, the composition comprising a combination of pheromonal agents, wherein the pheromonal agents comprise at least one steroid hormone and quinoline.

2. The composition of claim 1, wherein the steroid hormone is an androgen steroid selected from the group consisting of androstenone, androstenol, androstadienone, estratetraenol, and combinations thereof.

3. The composition of claim 2, wherein the androgen steroid consists of androstenone and androstenol.

4. The composition of claim 2, wherein the androgen steroid is present in an amount from between about 0.0001% to about 1% (w/w) of the composition.

5. The composition of claim 1, wherein quinoline is present in an amount from between about 0.0001% to about 1% (w/w) of the composition.

6. The composition of claim 1, wherein the composition further comprises a carrier solvent.

7. The composition of claim 6, wherein the carrier solvent is selected from the group consisting of lipophilic organic diluents, alcohols, ethylene glycol, propylene glycol, dipropylene glycol, ether, chloroform, benzene, carbon disulfide, oils including non-volatile and volatile liquids and oils, water, and combinations thereof.

8. The composition of claim 7, wherein the alcohol is selected from the group consisting of ethanol, propanol, isopropanol, butanol, pentanol, hexanol, heptanol, octanol, phenyl ethyl alcohol, and combinations thereof.

9. The composition of claim 1, wherein the composition further comprises an additional component selected from the group consisting of a surfactant, a thickener, a propellant, a fragrance, and combinations thereof.

10. A method of stimulating reproductive behavior and increasing reproductive success and productivity in a female suid comprising: administering a pheromone composition to the suid, the composition comprising a combination of pheromonal agents, wherein the pheromonal agents comprise at least one steroid hormone and quinoline, and wherein the amount of pheromonal agents administered to the animal is between about 1.0 ng/mL to about 1.0 g/mL.

11. The method of claim 10, wherein the suid is a sow.

12. The method of claim 10, wherein the method of administration is inhalation administration.

13. The method of claim 10, wherein the composition is formulated as a spray.

14. The method of claim 10, wherein administering the spray composition comprises spraying the suid or spraying the suid's environment with the composition.

15. A method of stimulating reproductive behavior and increasing reproductive success and productivity in a suid comprising: administering an effective amount of a pheromone spray composition to the suid, the spray composition comprising about 0.0004% (w/w) androstenone, about 0.0004% (w/w) androstenol, about 0.0004% (w/w) quinoline, about 5% (w/w) isopropanol, and about 91% (w/w) water.

16. The method of claim 15, wherein the suid is a sow.

* * * * *

UNITED STATES PATENT AND TRADEMARK OFFICE
CERTIFICATE OF CORRECTION

PATENT NO. : 9,480,689 B1
APPLICATION NO. : 14/943607
DATED : November 1, 2016
INVENTOR(S) : McGlone Page 1 of 1

It is certified that error appears in the above-identified patent and that said Letters Patent is hereby corrected as shown below:

On the Title Page

Item (73) please delete the Assignee:
"Animal Biotech, LLC, Dallas, TX (US)"
And insert:
-- Texas Tech University System, Lubbock, TX (US) --

Signed and Sealed this
First Day of January, 2019

Andrei Iancu
*Director of the United States Patent and Trademark Office*